(12) United States Patent
Green et al.

(10) Patent No.: US 7,682,824 B2
(45) Date of Patent: Mar. 23, 2010

(54) HOLDER FOR PCR SAMPLE COLLECTION AND PREPARATION

(75) Inventors: Douglas Jason Green, Baldwin, MD (US); Carrie Lynn Holmes, Belair, MD (US)

(73) Assignee: Smiths Detection Inc., Edgewood, MD (US)

( * ) Notice: Subject to any disclaimer, the term of this patent is extended or adjusted under 35 U.S.C. 154(b) by 887 days.

(21) Appl. No.: 10/852,684

(22) Filed: May 25, 2004

(65) Prior Publication Data

US 2005/0009071 A1    Jan. 13, 2005

Related U.S. Application Data

(63) Continuation-in-part of application No. 10/727,037, filed on Dec. 4, 2003, now Pat. No. 7,238,520.

(60) Provisional application No. 60/473,539, filed on May 28, 2003, provisional application No. 60/430,994, filed on Dec. 4, 2002.

(51) Int. Cl.
*C12M 1/26* (2006.01)

(52) U.S. Cl. .................................. 435/309.1

(58) Field of Classification Search ............... 435/309.1
See application file for complete search history.

(56) References Cited

U.S. PATENT DOCUMENTS

| 5,543,115 | A |  | 8/1996 | Karakawa |  |
| 6,180,395 | B1 | * | 1/2001 | Skiffington et al. | ...... 435/287.6 |
| 2002/0001539 | A1 | * | 1/2002 | DiCesare et al. | .............. 422/52 |

FOREIGN PATENT DOCUMENTS

EP    1024354 A1 *  8/2000

* cited by examiner

*Primary Examiner*—Walter D Griffin
*Assistant Examiner*—Lydia Edwards
(74) *Attorney, Agent, or Firm*—Foley & Lardner LLP

(57) ABSTRACT

A holder for PCR sample collection and preparation and method of using which has a buffer container housing removably connected to a plunger housing. A swab attached to an end of a plunger collects a sample of a specimen to be analyzed for biological warfare agents. The swab and plunger are inserted into the plunger housing, a buffer container is positioned inside the buffer container housing and the buffer container housing and plunger housing are attached. A buffer passes through the swab and elutes off the sample and the sample mixes with a reagent. The prepared sample loads into a reaction tube, by a whipping action, for analysis.

8 Claims, 6 Drawing Sheets

HOLDER FOR PCR SAMPLE COLLECTION AND PREPARATION

CROSS-REFERENCE TO RELATED APPLICATIONS

This application is a continuation-in-part of U.S. patent application Ser. No. 10/727,037 filed on Dec. 4, 2003, and accordingly is entitled to the benefit of U.S. Provisional Patent Application Ser. No. 60/430,994 filed on Dec. 4, 2002. This application also claims priority to and the benefit of U.S. Provisional Patent Application No. 60/473,539 filed on May 28, 2003. All three of the aforementioned applications are incorporated by reference herein in their entireties.

BACKGROUND

The application relates to a system designed to detect a polymerase chain reaction (PCR). The system includes devices that are designed to detect the presence or absence of a biological agent through DNA amplification. Detection is accomplished through heating and cooling a PCR reaction mixture located in a disposable reaction tube. The presence of an agent to be detected is indicated by an increase in fluorescence.

The present invention relates to a holder for polymerase chain reaction (PCR) collection and preparation comprising a buffer container housing operatively connectable to a plunger housing and a reaction tube.

The present invention pertains to collecting and preparing samples to be analyzed for the presence of a biological warfare agent (e.g., anthrax, tularemia, plague or smallpox) in the field, or on-site.

Conventional PCR collection and preparation require skill exceeding that of most field personnel. Typical PCR collection and preparation is a complicated procedure.

Conventional PCR collection and preparation require samples to be processed prior to analysis. A drawback to the sample collection and preparation is that it involves at least three complex steps. First, inhibitors such as humic acids and metals in the environment are removed. Second, the sample is filtered and concentrated. Third, a combination of reagents required by the PCR assay is added to the sample.

Another drawback of conventional PCR collection and preparation is the work is generally performed at a lab, not in the field. Typically, such collection and preparation is not portable for use in the field for on-site testing of biological warfare agents.

SUMMARY OF THE INVENTION

According to an embodiment of the present invention, an apparatus for collecting and preparing samples for PCR analysis is provided. The apparatus includes a buffer container housing and a plunger housing. The buffer container housing includes a buffer container positioned inside the buffer container housing. The plunger housing includes a plunger configured to be positioned inside the plunger housing. A swab is attached to an end of the plunger and a reaction tube is attached to an end of the plunger housing. The buffer container housing is configured to be operatively connected to the plunger housing.

According to another aspect of the present invention, a PCR analysis preparation method is provided. The method includes the steps of providing a device comprising a swab and a plunger and wiping the swab over a test surface to collect a sample. The PCR analysis preparation method further includes inserting the swab into a buffer container by using a twisting action between a plunger housing and a buffer container housing to attach the plunger housing to the buffer container housing, thereby enabling a buffer to be released and pass through the swab and allowing the buffer and sample to pass into a chamber for mixing with a reagent mixture. The method further includes whipping the device, thereby loading a prepared sample into a reaction tube.

It is to be understood that both the foregoing general description and the following detailed description are exemplary and exemplary only and are not restrictive of the invention as claimed.

BRIEF DESCRIPTION OF THE DRAWINGS

These and other features, aspects, and advantages of the present invention will become apparent from the following description, appended claims, and the accompanying exemplary embodiments shown in the drawings, which are briefly described below.

FIG. 2($b$) is a side view of the buffer container housing of FIG. 1.

FIG. 3($b$) is a side view of the swab support of FIG. 1.

FIG. 4($b$) is a cross-sectional view of the plunger housing of FIG. 1. FIG. 4($c$) is a side view of the plunger housing of FIG. 1.

FIG. 5($b$) is a side view of the reaction tube of FIG. 1. FIG. 5($c$) is a cross-sectional view of the reaction tube of FIG. 1.

DESCRIPTION

Hereinafter, embodiments of the present invention will be described with reference to the attached drawings.

Figure 1:
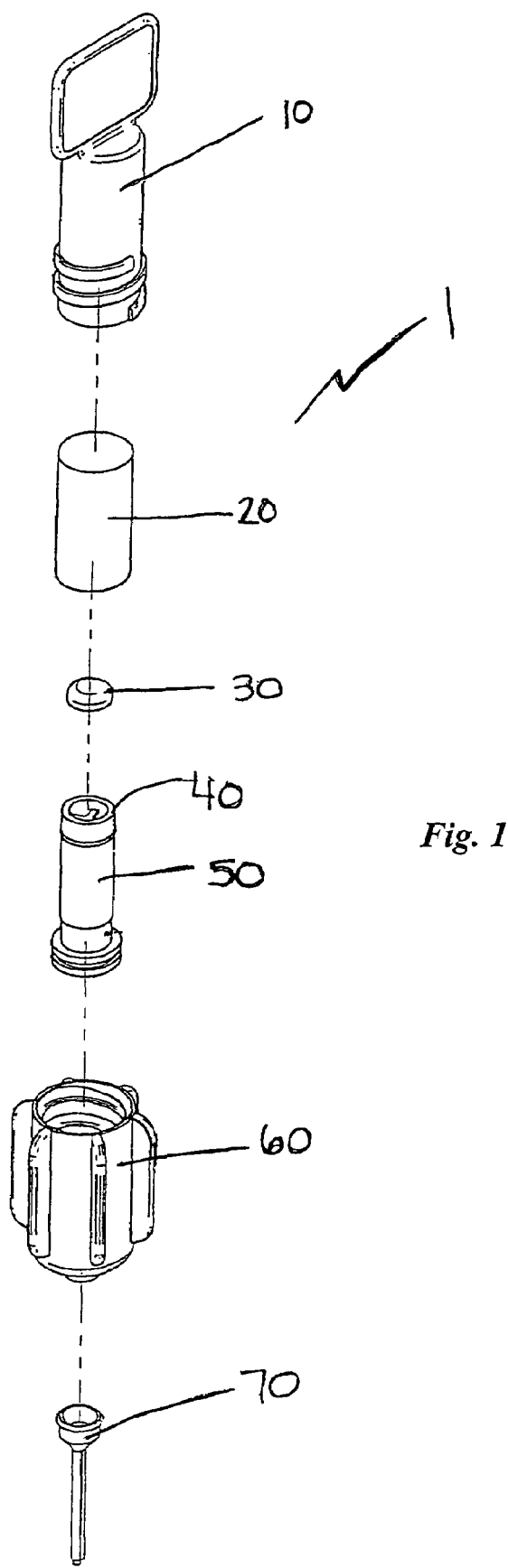
FIG. 1 is an exploded view of an embodiment of an apparatus for collecting and preparing samples for PCR analysis.

An apparatus 1 for collecting and preparing a sample for PCR analysis, to determine the presence or absence of a biological agent (e.g. anthrax, tularemia, plague or smallpox), is disclosed in FIG. 1. The apparatus 1 includes a buffer container housing 10 operatively connected to a plunger housing 60, a buffer container 20, a plunger 50, a swab 30, a swab support 40 and a reaction tube 70.

Figures 2A, 2B:
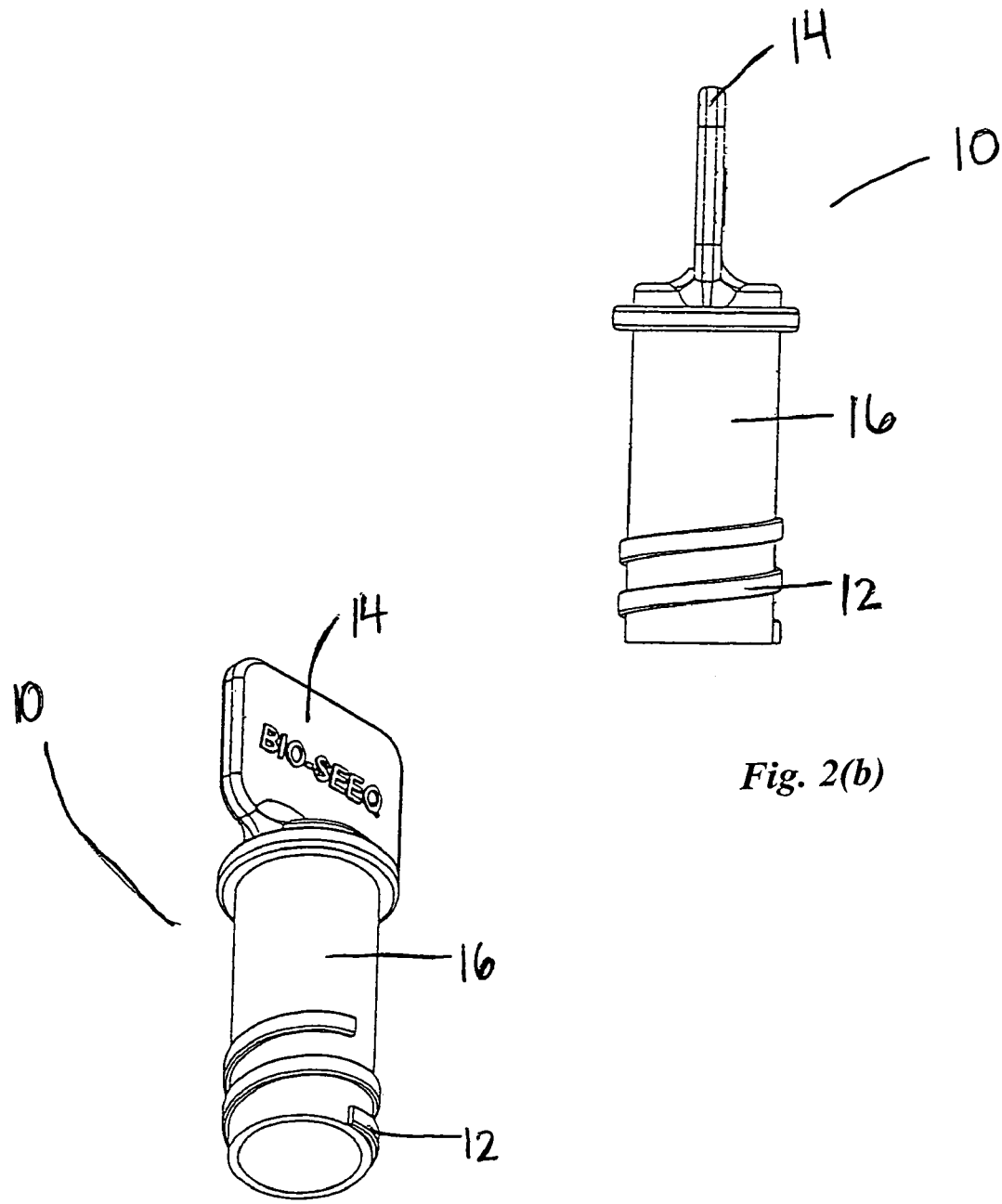
FIG. 2($a$) is a perspective view of the buffer container housing of FIG. 1.

As can be seen in FIGS. 2($a$) and 2($b$), the buffer container housing 10 includes a tab 14 at an end of a cylindrical housing portion 16. The cylindrical housing portion 16 includes outwardly protruding threads 12. The threads 12 are configured to correspond with threaded grooves 62 on the plunger housing 60, as can be seen in FIGS. 4($a$), 4($b$). The tab 14 is configured to aid the user in twisting or screwing the buffer container housing 10 together with the plunger housing 60.

The buffer container 20 may be any suitable container for containing a buffer, such as a Whatman Mini UniPrep brand buffer chamber 20.

Figure 3A:
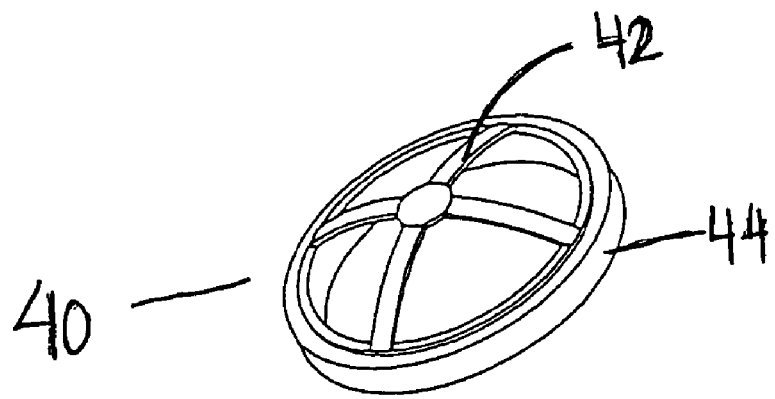
FIG. 3($a$) is a perspective view of the swab support of FIG. 1.
Figure 3B:
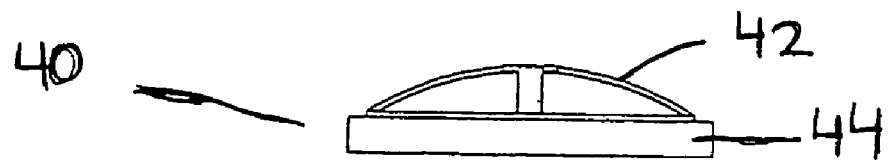

The swab or swabbing matrix 30, shown in FIG. 1, is attached to an end of the plunger 50. A swab support 40 supports the swab 30 on the plunger 50. As can be seen in FIGS. 3($a$) and 3($b$), the swab support 40 includes a convex framework 42 and a frame 44. The frame 44 may be generally circular. The convex framework 42 is positioned inside the frame 44, and is configured in such a manner to ensure that the swab 30 protrudes away from the plunger 50 and engages with the surface upon which the sample is to be collected for analysis.

The swab 30 is configured to collect a sample of a specimen for PCR analysis to determine the presence or absence of a biological agent. The swab 30 may be formed in a dome shape.

The swab 30 may be made of a filter like material, or any other suitable material for collecting material to be analyzed such as, for example, IsoCode paper.

Figure 4A:
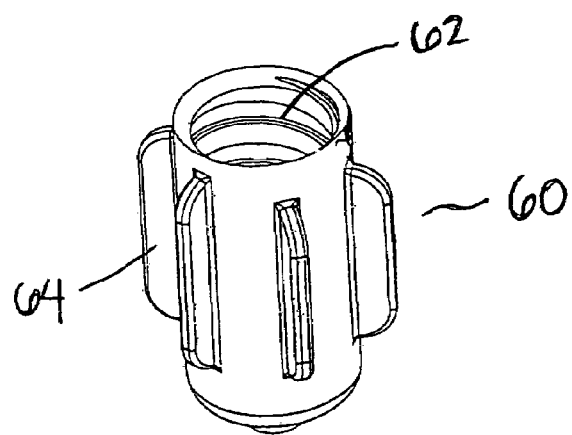
FIG. 4($a$) is a perspective view of the plunger housing of FIG. 1.
Figure 4B:
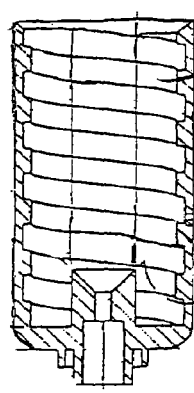
Figure 4C:
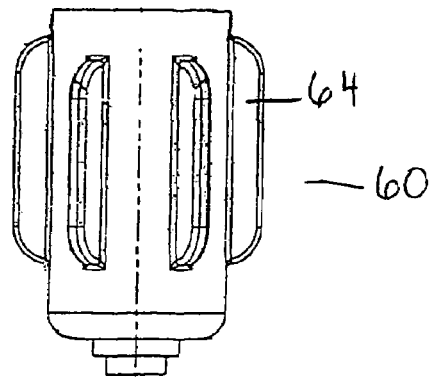

As can be seen in FIGS. 4(a), 4(b), 4(c), the plunger housing 60 includes threaded grooves 62 in an interior surface of the plunger housing 60. The plunger housing 60 may be cylindrical in shape. Radial extending tabs 64 may protrude from an outer surface of the plunger housing 60. The radial extending tabs 64 ensure: (1) that the reaction tube 70 properly engages with a slot in a detector for further analysis of a sample (not shown) and (2) that the device can be handled properly with heavy hazardous material gloves.

The plunger 50, shown in FIG. 1, with the attached swab 30 and swab support 40 may be positioned inside of the plunger housing 60. Reagent beads (not shown) such as, for example, ceramic mixing beads, may be positioned inside of an inner chamber (not shown) of the plunger 50.

The plunger 50 may comprise a Whatman Mini UniPrep brand plunger 50, or any other suitable plunger 50.

Figure 5A:
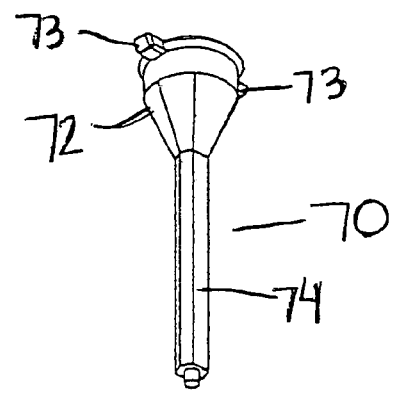
FIG. 5($a$) is a perspective view of the reaction tube of FIG. 1.
Figure 5B:
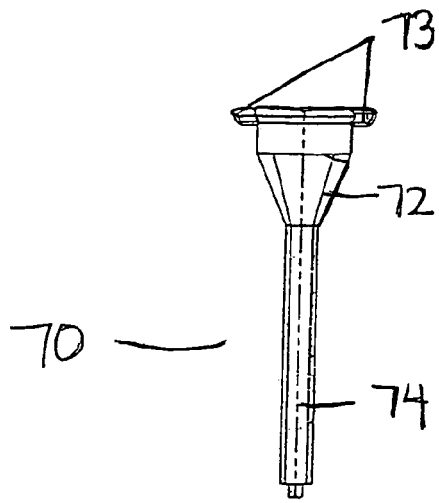
Figure 5C:
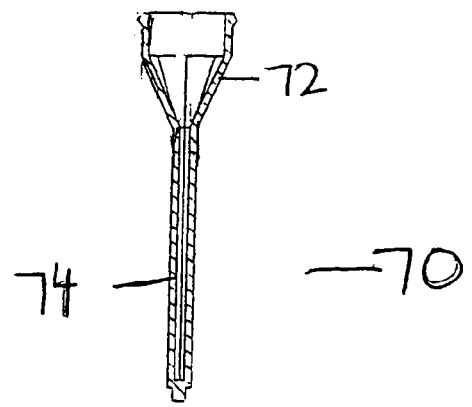

As can be seen in FIGS. 5(a), 5(b), and 5(c), the reaction tube 70 includes a tube portion 74 and a cup portion 72 at an end of the tube portion 74. Alignment tabs 73 extend from the brim of the cup portion 72. The alignment tabs 73 are configured to ensure that the reaction tube 70 is properly attached, aligned and retained to the plunger housing 60.

The reaction tube 70 may comprise any suitable tube for holding a prepared sample for further analysis, such as a Bio-Seeq brand reaction tube 70. The reaction tube 70 may be disposable.

The apparatus 1 may be employed to swab surfaces that may be contaminated with biological warfare agents. The swab 30, attached to an end of the plunger 50, of the apparatus 1 collects a sample of the possible contaminate and is then inserted into the buffer container 20. The swab 30 is inserted into the buffer container 20 by a twisting action between the plunger housing 60 and the buffer container housing 10. The rate at which the swab 30 is positioned inside the buffer container 20 is controlled by the twisting action; which therefore controls the rate at which the buffer contained in the buffer container 20 passes through the swab 30 and elutes or washes off the sample. The sample and buffer pass into the inner chamber, thus rehydrating the lyophilized reagent beads, which are then mixed with the sample. The sample is then prepared for analysis and loaded into the reaction tube 70. The sample passes into the reaction tube 70 by a whipping action. The user of the apparatus 1 whips the apparatus 1 several times to force the prepared sample into the reaction tube 70. The reaction tube 70, which is attached to apparatus 1, is then ready to be placed inside a hand-held detector for analyzing the sample.

The apparatus 1 may be constructed of a suitable size and weight so that it may be easily transported for use in the field. For example, the apparatus 1 may be carried in the operator's hand for simple portability.

In an alternative embodiment, the buffer container 20 includes a film 22 (not shown) that covers an end of the buffer container 20. The plunger 50 and swab 30 rupture the film 22 by the twisting action forcing the swab 30 into the buffer container 20. When the film 22 is ruptured, a buffer (not shown) is released out of the buffer container 20 to pass through the swab 30 and elute off the sample.

Figure 6:
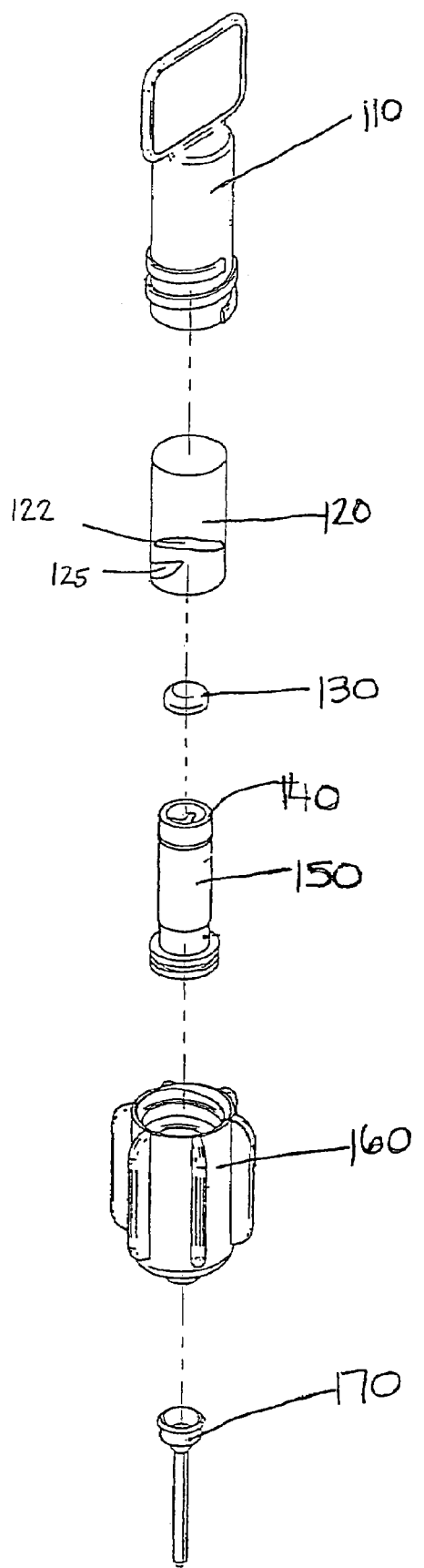
FIG. 6 is an exploded view of another embodiment of an apparatus for collecting and preparing samples for PCR analysis.

In an alternative embodiment shown in FIG. 6, a spike 125 is positioned between the swab 130 and buffer container 120.

The spike 125 is configured to rupture the film 122 covering the buffer container 120 to allow a buffer to be released from the buffer container 120 and flow through the swab 130. The spike 125 ruptures the film 122 covering the buffer container 120 by the forcing of the spike 125 into the buffer container 120 by the twisting action between the buffer container housing 110 and plunger housing 160.

In another alternative embodiment, the swab 30 may be covered by a mesh 32 (not shown). Alternatively, the swab 30 may cover the mesh 32.

The apparatus may contain an additive that improves visibility of the combined sample-reagent mixture prior to introduction to the instrument such as, for example, an indicating chemical dye. This dye may also be sensitive to the reagent materials such that it appears one color prior rehydration of the reagent beads with the sample and another color after the sample has been thoroughly mixed with the reagents. Another feature of the dye is that the color change may be used to indicate that the pH of the unknown sample is not compatible with the reagent system prior to PCR processing. In the preferred embodiment, Cresol Red, chemical formula $C_{21}H_{18}O_5S$, is placed in the buffer. The normal color of this material in a neutral solution is yellow. When properly mixed with the PCR reagents, the solution will appear violet to red. Should the reagents not be present for any reason or if the sample is has an incorrect pH, the buffer will appear yellow indicating a problem with the reaction.

Given the disclosure of the present invention, one versed in the art would appreciate that there may be other embodiments and modifications within the scope and spirit of the invention. Accordingly, all modifications attainable by one versed in the art from the present disclosure within the scope and spirit of the present invention are to be included as further embodiments of the present invention. The scope of the present invention is to be defined as set forth in the following claims.

What is claimed is:

1. A Polymerase Chain Reaction analysis preparation method comprising:
   providing a device including a swab and a plunger and wiping the swab over a test surface to collect a sample;
   inserting the swab into a buffer container by using a twisting action between a plunger housing and a buffer container housing to attach the plunger housing to the buffer container housing, thereby enabling a buffer to be released and pass through the swab and allowing the buffer and sample to pass into a chamber for mixing with a reagent mixture; and
   whipping the device, thereby loading a prepared sample into a reaction tube.

2. The method of claim 1, wherein the swab comprises a filter material.

3. The method of claim 1, wherein the buffer container comprises at least one mixing bead.

4. The method of claim 1, wherein the buffer container comprises a film covering an end of the buffer container.

5. The method of claim 4, wherein inserting the swab into the buffer container causes the film covering an end of the buffer container to rupture.

6. The method of claim 4, wherein a spike positioned between the buffer container and the swab causes the film to rupture.

7. The method of claim 1, wherein the swab is covered by a mesh.

8. The method of claim 1, wherein the buffer contains an indicating dye that changes color of the reagent is present and correctly mixed.

* * * * *